US005817899A

United States Patent [19]
Hope et al.

[11] Patent Number: 5,817,899
[45] Date of Patent: Oct. 6, 1998

[54] POLYALPHAOLEFIN DIMERS HAVING LOW KINEMATIC VISCOSITIES

[75] Inventors: Kenneth D. Hope; Ting C. Ho; Barrett L. Cupples, all of Kingwood, Tex.

[73] Assignee: Chevron Chemical Company, San Ramon, Calif.

[21] Appl. No.: 876,778

[22] Filed: Jun. 16, 1997

Related U.S. Application Data

[63] Continuation of Ser. No. 435,935, May 5, 1995, abandoned, which is a continuation-in-part of Ser. No. 298,635, Aug. 31, 1994, Pat. No. 5,550,307, which is a continuation-in-part of Ser. No. 217,265, Mar. 24, 1994, Pat. No. 5,420,373.

[51] Int. Cl.[6] ............................... C07C 9/00; C07C 2/02
[52] U.S. Cl. ............................... 585/16; 585/510
[58] Field of Search ............... 585/16, 525, 516, 585/518, 510, 511

[56] References Cited

U.S. PATENT DOCUMENTS

| | | | |
|---|---|---|---|
| 3,769,363 | 10/1973 | Brennan | 260/683.15 B |
| 3,997,621 | 12/1976 | Brennan | 260/683.15 B |
| 4,218,330 | 8/1980 | Shubkin | 252/46.6 |
| 4,436,947 | 3/1984 | Morganson et al. | 585/525 |
| 4,982,026 | 1/1991 | Karn et al. | 585/18 |
| 5,068,487 | 11/1991 | Theriot | 585/10 |
| 5,171,905 | 12/1992 | Theriot et al. | 585/10 |
| 5,171,918 | 12/1992 | Shubkin et al. | 585/510 |

OTHER PUBLICATIONS

Reid, Robert C., Prausnitz, John M., Sherwood, Thomas K., *The Properties of Gases and Liquids*, 1977, pp. 439–440.

*Primary Examiner*—Glenn Caldarola
*Assistant Examiner*—In Suk Bullock
*Attorney, Agent, or Firm*—W. Bradley Haymond

[57] ABSTRACT

A dimer composition has an improved low temperature viscosity if it has less than a certain amount of normal paraffin. A 1-octene dimer should have less than 0.50 wt. % normal hexadecane, a 1-decene dimer should have less than 0.05 wt. % normal eicosane, a 1-dodecene dimer should have less than 0.60 wt. % normal tetracosane, and a 1-tetradecene dimer should have less than 0.10 wt. % normal octacosane.

6 Claims, 2 Drawing Sheets

POLYALPHAOLEFIN DIMERS HAVING LOW KINEMATIC VISCOSITIES

This application is a continuation of Ser. No. 435,935, filed May 5, 1995, abandoned, which is a continuation-in-part of application Ser. No. 08/298,635, filed Aug. 31, 1994, entitled "Increased Dimer Yield of Olefin Oligomers Through Catalyst Modifications," now Pat. No. 5,550, 307, which is a continuation-in-part of application Ser. No. 08/217,265, filed Mar. 24, 1994, now U.S. Pat. No. 5,420, 373, entitled "Controlled Formation of Olefin Oligomers." Both application Ser. Nos. 08/298,635 and 08/217,265 are hereby incorporated by reference for all purposes.

The present invention relates to a process of producing dimers of olefins having improved low temperature quality.

BACKGROUND OF THE INVENTION

It is well known to make polyalphaolefins by reacting 1-decene with boron trifluoride and butanol. The oligomer product is a mixture of dimer, trimer, and higher molecular weight materials. Dimers having good low temperature properties are useful in avionics coolants, dielectric fluids, and heat transfer fluids.

U.S. Pat. Nos. 5,068,487; 5,171,905; and 5,171,918 disclose a process for producing predominately dimer and trimer. That process uses boron trifluoride in conjunction with alcohol alkoxylates

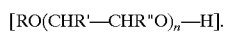
[RO(CHR'—CHR"O)$_n$—H].

Previously, we filed an application U.S. Ser. No. 08/217, 265 to the use of boron trifluoride in conjunction with hydroxy carbonyls. In one embodiment of that invention, a ketone was used as a copromoter with the hydroxy carbonyl to improve dimer yield.

We also filed an application U.S. Ser. No. 08/298,635 to the use of boron trifluoride in conjunction with an alcohol alkoxylate and a ketone.

Other patents of interest are U.S. Pat. Nos. 3,769,363: 3,997,621; 4,218,330; 4,436,947; and 4,982,026.

U.S. Pat. No. 3,769,363 by Brennan discloses oligomerization of $C_6$-$C_{12}$ normal α-olefins, such as 1-decene, with boron trifluoride and $C_5$ carboxylic acid to improve trimer yields.

U.S. Pat. No. 3,997,621 by Brennan discloses oligomerization of $C_6$-$C_{12}$ normal α-olefins using alcohols or water promoters in conjunction with small amounts of methyl and ethyl esters of a $C_2$-$C_5$ mono carboxylic acid to improve trimer yields.

U.S. Pat. No. 4,218,330 by Shubkin discloses dimerization of a $C_{12}$-$C_{18}$ monomer with a boron trifluoride-water complex and an excess of boron trifluoride. The product is distilled to remove the monomer and is hydrogenated for use as a crankcase lubricant. This product is mainly dimers, with minor amounts of trimers and higher oligomers.

U.S. Pat. No. 4,436,947 by Morganson et al. discloses oligomerization of $C_6$–$C_{20}$ olefins, such as 1-decene, with boron trifluoride and a mixture of an aliphatic alcohol, an aliphatic ketone, and a polyol. This product is predominately trimer.

U.S. Pat. No. 4,982,026 by Karn et al. discloses polymerization of lower alkene monomers ($C_2$-$C_6$) with boron trifluoride and a strong acid, such as phosphoric acid, to produce a polymer having a molecular weight from 250 to 500 and having a high vinylidene content.

U.S. Pat. Nos. 3,769,363: 3,997,621; 4,218,330; 4,436, 947; 4,982,026; 5,068,487; 5,171,905; and 5,171,918 are hereby incorporated by reference for all purposes.

SUMMARY OF THE INVENTION

We have identified what causes poor low temperature performance for hydrogenated dimers. The poor quality dimers have crystals that form at low temperatures. We cooled a poor quality dimer slowly until the crystals began to form, then separated the crystals from the dimer and analyzed the crystals.

Surprisingly, for the dimer 1-decene ($C_{10}$), the crystals were substantially normal eicosane ($C_{20}$), with lesser amounts of normal nonadecane ($C_{19}$) and normal octadecane ($C_{18}$), and trace amounts of normal heneicosane ($C_{21}$), normal heptadecane ($C_{17}$), normal docosane ($C_{22}$). When those crystals were dissolved in good dimer, the viscosity increased.

By adjusting operating parameters to reduce the presence of normal hexadecane ($C_{16}$) in 1-octene ($C_8$) dimer to less than 0.50 wt. %, we were able to achieve a −54° C. viscosity of less than 280 cSt. By adjusting operating parameters to reduce the presence of normal eicosane in 1-decene dimer to less than 0.05 wt. %, we were able to achieve a −54° C. viscosity of less than 1000 cSt and a −40° C. viscosity of less than 240 cSt. By adjusting operating parameters to reduce the presence of normal octacosane ($C_{28}$) in 1-tetradecene ($C_{14}$) dimer to less than 0.10 wt. %, we were able to achieve a −20° C. viscosity of less than 1000 cSt.

In order to reduce the amounts of these normal paraffins, the amount of the normal paraffins and corresponding normal olefins in the feed to the hydrogenation unit should be limited. Prior to hydrogenation, a 1-octene dimer should have less than 0.50 wt. % normal $C_{16}$ materials, 1-decene dimer should have less than 0.05 wt. % normal $C_{20}$ materials, 1-dodecene dimer should have less than 0.60 wt. % normal $C_{22}$ materials, and a 1-tetradecene dimer should have less than 0.10 wt. % normal $C_{24}$ materials.

BRIEF DESCRIPTION OF THE DRAWINGS

In order to assist the understanding of this invention, reference will now be made to the appended drawings. The drawings are exemplary only, and should not be construed as limiting the invention.

DETAILED DESCRIPTION OF THE INVENTION

Figure 1A:
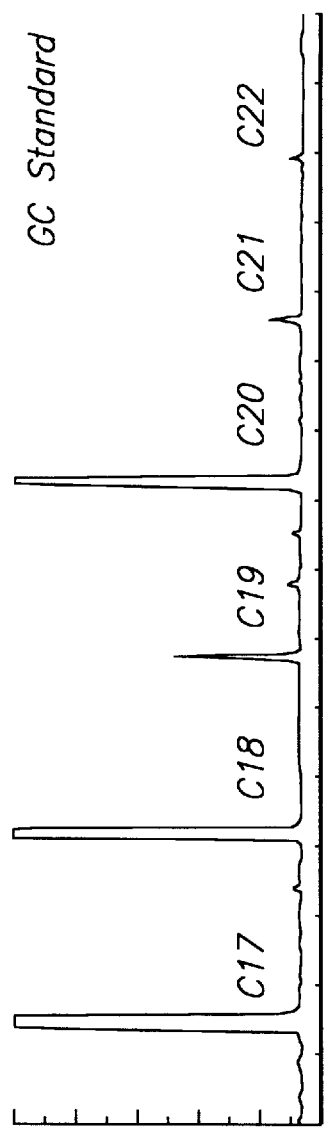
FIG. 1 is a comparison of the gas chromatography results of the crystals discussed in Example 5 and a gas chromatography standard which contains straight chain saturated hydrocarbons. The peaks are labeled from $C_{17}$ to $C_{22}$, which correspond to heptadecane to docosane.

In its broadest aspect, the present invention involves achieving low temperature viscosities in oligomers by reducing the presence of certain normal paraffins to less than certain amounts in the dimer. For 1-octene dimer, the amount of normal hexadecane should be reduced to less than 0.50 wt. %. For 1-decene dimer, the amount of normal eicosane should be reduced to less than 0.05 wt. %. For 1-dodecene dimer, the amount of normal tetracosane should be reduced to less than 0.60 wt. %. For 1-tetradecene dimer, the amount of normal octacosane should be reduced to less than 0.10 wt. %.

The oligomerization of the olefinic monomer can be performed by contacting that monomer with boron trifluoride and a promoter, such as a hydroxy carbonyl promoter. The promoter can be used in conjunction with a secondary promoter.

Olefinic Monomer

Preferably, olefins used in making the oligomer are predominately (at least 50 mole %) $C_6$-$C_{20}$ straight-chain, mono-olefinically unsaturated hydrocarbons in which the olefinic unsaturation occurs at the 1- or α-position of the straight carbon chain. Straight-chain α-olefins are preferred because they are more reactive and commercially available. Such α-olefins can be made by the thermal cracking of paraffinic hydrocarbons or by the well known Ziegler ethylene chain growth and displacement on triethyl aluminum. Individual olefins may be used, as well as mixtures of such olefins. Examples of such olefins are 1-hexene, 1-heptene, 1-octene, 1-nonene, 1-decene, 1-dodecene, 1-hexadecene and 1-tetradecene. The more preferred normal α-olefin monomers are those containing about 8 to 14 carbon atoms. The olefin monomers can also contain minor amounts of up to about 50 mole %, and usually less than 25 mole %, of internal olefins and vinylidene olefins.

Oligomer Product

The oligomer product is that portion of the reaction product remaining after boron trifluoride, promoters, and unreacted monomer are removed. A 1-octene dimer should have less than 0.50 wt. % normal hexadecane to have a –54° C. viscosity of less than 280 cSt. A 1-decene dimer should have less than 0.05 wt. % normal eicosane to have a –54° C. viscosity of less than 1000 cSt and a –40° C. viscosity of less than 240 cSt. A 1-tetradecene dimer should have less than 0.10 wt. % normal octacosane to have a –20° C. viscosity of less than 1000 cSt.

Oligomerization Reaction

The promoters are used in minor but effective amounts. For example, the total amount of promoters used can be from about 0.001 to 0.04 moles per mole of monomer (0.1 to 4.0 mole percent). In general, boron trifluoride is used in molar excess to the amount of promoter. This can be accomplished by using a closed reactor and maintaining a positive boron trifluoride pressure over the reaction mixture. The promoter can be mixed with the olefin feed and the reaction can be carried out in a batch or continuous process at temperatures of about 0° to 200° C. and pressures ranging from atmospheric up to, for example, 1,000 psig. The reaction temperature will change the oligomer distribution, with increasing temperatures favoring the production of dimers. Preferred reaction temperatures and pressures are about 20° to 90° C. and 5 to 100 psig.

When a desired oligomer distribution is reached in the batch mode, the reaction is terminated by venting off excess boron trifluoride gas and purging with nitrogen gas to replace all boron trifluoride gaseous residue. The reaction product, unreacted monomer, and boron trifluoride-promoter complex residue are removed from the reactor for further processing. In the continuous mode the dissolved boron trifluoride may be degassed. The boron trifluoride-promoter complex may be separated by settling or coalescing from the reaction product.

The crude reactor product is then washed with an aqueous caustic solution and followed by one or more water washes to ensure neutralization.

The oligomer mixture from the reaction contains monomer, which can be removed by distillation. The monomer has been found to contain appreciable amounts of less reactive, isomerized material. However, this monomer can be recycled because it will react to form oligomers in the presence of fresh α-olefin monomer. The product mixture can be further separated by distillation to provide one or more product fractions having the desired viscosities for use in various lubricant applications such as avionics coolants, dielectric fluids, heat transfer fluids, drilling, hydraulic or metal working fluids, gear oils and crankcase lubricants.

The oligomer product can be hydrogenated by conventional methods to increase the oxidation stability of the product. Supported nickel catalysts are useful. For example, nickel on a Kieselguhr support gives good results. Batch or continuous processes can be used. For example, the catalyst can be added to the liquid and stirred under hydrogen pressure or the liquid may be trickled through a fixed bed of the supported catalyst under hydrogen pressure. Hydrogen pressures of about 100 to 1,000 psig at temperatures of about 150° to 300° C. are especially useful. Preferably, the hydrogen pressure is from 400 to 1,000 psig and the maximum temperature is 200° C. to 300° C.

The amount of paraffin present in the product may be limited by preventing cracked fragments from being recycled to the reactor and eventually ending up in the dimer fraction. Typically, unreacted monomers and dimers are recycled to the reactor to increase the process efficiency or to produce a heavier oligomer distribution. Thermal degradation in the separational stage(s) or hydrocracking in the hydrogenator can result in cracking of higher molecular weight oligomers. These cracked fragments can migrate into the product stream. Generally, hydrocracking begins to occur with some severity at temperatures above 300° C., but may even occur to a lesser degree at lower temperatures. For example, in the production of a $C_{10}$ dimer, the cracked fragments in a molecular weight range from $C_{17}$ to $C_{22}$ will normally appear in the dimer fraction. Upon hydrogenation, some of the cracked fragments will become straight chain saturated hydrocarbons which can adversely affect the low temperature viscosity. The presence of the cracked fragments is supported by the fact, as discussed in Example 5, the crystals are composed of $C_{17}$ to $C_{22}$ hydrocarbons. Odd-carbon numbers cannot be synthesized from 1-decene oligomerization. Even-carbon numbers other than $C_{20}$ are also unlikely to be formed from 1-decene oligomerization. Therefore, carbon numbers other than $C_{20}$ are most likely formed from cracking of higher molecular weight oligomers.

The reaction conditions that are chosen may also affect the levels of the straight chain $C_{20}$ compounds. Favorable conditions may be obtained by selecting promoters such as hydroxy ketones, alcohol alkoxylates and alcohols as opposed to unfavorable promoters such as peroxides or $SiO_2 \cdot 12WO_3$. Shorter residence times (less than 90 minutes, preferably less than 45 minutes) and lower reaction temperatures also favor lower amounts of the normal paraffins and desirable low temperature viscosities. Finally, in order to achieve reduced amounts of cracked fragments and subsequent normal paraffins, the dimer recycle should be eliminated.

Hydroxy Carbonyl Promoter

By "hydroxy carbonyl," we mean an organic compound having both a hydroxyl group (containing an —OH unit) and a carbonyl group (either ketone or aldehydes).

Preferably, the hydroxy carbonyl is a hydroxy ketone because of concerns of unavailability, odor, and instability of hydroxy aldehydes. Preferably the hydroxyl group is either methyl hydroxyl, ethyl hydroxyl, propyl hydroxyl, butyl hydroxyl, pentyl hydroxyl, or hexyl hydroxyl, with the alkyl group being either straight or branched. Preferably the ketone group is either methyl ketone or ethyl ketone.

The hydroxy carbonyl can have more than one hydroxyl group and can have more than one carbonyl group. The compounds can have alternating hydroxyl and carbonyl groups (e.g., 4-hydroxy-4-methyl-2,6-heptanedione), or similar groups can be grouped together (e.g., 6-hydroxy-6-methy-2,4-heptanedione). Neither the hydroxyl groups nor the carbonyl groups have to be the same throughout the molecule. For instance, in a dione compound, the carbonyl groups could be both methyl-ketone and ethyl-ketone (e.g., 4-hydroxy-4-methyl-2,6-octanedione).

More than one hydroxy ketone can be used. For instance, in one preferred embodiment, 1-hydroxy-2-butanone and 4-hydroxy-4-methy-2-pentanone are used together.

The ratio of hydroxyl groups to carbonyl groups is preferably 1:1, (e.g., 4-hydroxy-4-methyl-2-pentanone). That ratio can be higher or lower. For instance, other hydroxy ketones conceived to be part of this invention include 2,6-dihydroxy-2,6-dimethyl-4-heptanone (ratio of 2:1) and 4-hydroxy-4-methyl-2,6-heptanedione (ratio of 1:2).

Suitable hydroxy ketones include, but are not limited to, hydroxy acetone, 1-hydroxy-2-butanone, 3-hydroxy-2-butanone, 4-hydroxy-2-butanone, 3-hydroxy-3-methyl-2-butanone, 3-hydroxy-2-pentanone, 4-hydroxy-2-pentanone, 1-hydroxy-3-pentanone, 2-hydroxy-3-pentanone, 3-hydroxy-3-methyl-2-pentanone, 3-hydroxy-4-methyl-2-pentanone, 4-hydroxy-3methyl-2-pentanone, 4-hydroxy-4-methyl-2-pentanone, 2-hydroxy-2-methyl-3-pentanone, 3-hydroxy-2-hexanone, 4-hydroxy-2-hexanone, 4-hydroxy-3-hexanone, 5-hydroxy-3-hexanone, 4-hydroxy-4-methyl-3-hexanone, 4-hydroxy-5-methyl-3-hexanone, 5-hydroxy-4-methyl-3-hexanone, 5-hydroxy-5-methyl-3-hexanone, 4-hydroxy-3-heptanone, and 5-hydroxy-3-heptanone.

Preferably, the hydroxyl group is attached to a tertiary carbon, such as in 3-hydroxy-3-methyl-2-butanone, 3-hydroxy-3-methyl-2-pentanone, 4-hydroxy-4-methyl-2-pentanone, 2-hydroxy-2-methyl-3-pentanone, 4-hydroxy-4-methyl-3-hexanone, 5-hydroxy-5-methyl-3-hexanone. Of these hydroxy ketones, the preferred hydroxy ketones are β-hydroxy ketones, such as 4-hydroxy-4-methyl-2-pentanone and 5-hydroxy-5-methyl-3-hexanone.

A preferred hydroxy carbonyl is 4-hydroxy-4-methyl-2-pentanone because it gives no emulsion in the reactor or in the water wash, as discussed below. 1-hydroxy-2-butanone gives a slight emulsion in the water wash and hydroxy acetone gives a significant emulsion in the water wash. In general, we have found that tertiary hydroxy ketones, such as, 4-hydroxy-4-methyl-2-pentanone and 3-hydroxy-3-methyl-2-butanone form no, or appreciably lesser amounts of, emulsion than secondary or primary hydroxy ketones. Secondary hydroxy ketones, such as, 3-hydroxy-2-butanone appear to form more dimer than the corresponding primary hydroxy ketones, such as, 1-hydroxy-2-butanone. Also, higher conversion rates have been observed with α-hydroxy ketones versus β-hydroxy ketones.

Secondary Promoters

In one embodiment, a second promoter can be used in conjunction with the boron trifluoride and the primary promoter. Possible secondary promoters include aldehydes, alcohols, alcohol alkoxylates, carboxylic acids, ethers, ketones, and their mixtures. These secondary promoters are used to further initiate oligomerization.

Preferably an alcohol, such as methanol, is used as a secondary promoter to achieve a faster reaction rate. The amount of alcohol or alcohol alkoxylate used depends, in part, on the ratio of hydroxyl groups to carbonyl groups in the hydroxy carbonyl. Less secondary promoter is needed if this ratio is high (i.e., if there is an excess of hydroxyl groups to carbonyl groups).

Alcohol alkoxylates useful as secondary promoters can be represented, for example, by the formula:

where R is hydrocarbyl containing from 1 to 24 carbons, including mixtures thereof, R' and R" are independently hydrogen, methyl, or ethyl, and n averages 1 to 15. Such alcohol alkoxylates are disclosed in U.S. Pat. No. 5,068,487, entitled "Olefin Oligomerization With BF3 Alcohol Alkoxylate Co-Catalysts," which is hereby incorporated by reference for all purposes.

A ketone, such as methyl-ethyl-ketone, can also be used as a secondary promoter to suppress the formation of higher oligomers.

EXAMPLES

The invention will be further illustrated by the following examples, which set forth particularly advantageous method embodiments. While the Examples are provided to illustrate the present invention, they are not intended to limit it.

Gas Chromatography Method For Oligomer Distribution

Hewlett-Packard Model 5890 series II gas chromatograph was used to analyze oligomer distribution in all the examples presented. The instrument had a Chrompack Ultimetal HT SimDist CB 10 m×0.5 mm ID column with a 0.15 μm stationary phase film thickness. The instrument was set up in the following oven temperature profile:

Initial temperature—60° C.

Ramp up rate—16° C. per minute

Final temperature —435° C.

Final time—12 minutes

Carrier—Helium

Flow rate—5 ml/min

Flame Ionization Detector

Cool on-column injection 0.2 μl injection volume

Gas Chromatography Method For Percent Paraffin

Hewlett-Packard Model 5890 series II gas chromatograph was used to analyze paraffin content in all the examples presented. The instrument had a 30 m×0.25 mm ID column with a SE-30 0.25 μm stationary phase film thickness. The instrument was set up in the following oven temperature profile:

Initial temperature—100° C.

Initial time—1 minute

Ramp up rate—6° C. per minute

Final temperature—300° C.

Final time—10 minutes

Example 1

$C_{10}$ Dimer

The oligomerization reaction was carried out in either an autoclave reactor or a continuous reactor train. The autoclave reactor was equipped with a packless stirrer, and all wetted surfaces were made of 316 stainless steel. The reactor had an external electrical heater and an internal cooling coil for temperature control. The reactor was equipped with a dip tube, gas inlet and vent valves, and a pressure relief rupture disc. Prior to the monomer charge, the reactor was cleaned, purged with nitrogen and tested for leaks.

One thousand grams of 1-decene was charged into the batch reactor. The promoter, acetol, was added to a concentration of 0.25 wt. % based on feed. The entire reactor content was heated under nitrogen blanket to reach 60° C. When the reactor temperature reached equilibrium, the reactor was then evacuated to remove the nitrogen. Boron trifluoride gas was then sparged slowly with agitation in addition to temperature control via a cooling coil to avoid reactor temperature overrun. Additional boron trifluoride was added as necessary to maintain a reactor pressure of 30 psig. The reaction was terminated after two hours by venting off excess boron trifluoride gas and purging with nitrogen. The reaction product was then washed with a 4 wt. % aqueous sodium hydroxide solution followed by several water washes to ensure neutralization. The product was saved for further treatments such as hydrogenation and fractionation. The resultant dimer fraction generally had a 97+% purity based on the gas chromatography method for oligomer distribution.

The continuous monomer feed reactor was equipped with monomer, promoter and gas inlet ports, vent valves, and a pressure relief rupture disc. Prior to start-up, the reactor was cleaned, purged with nitrogen and tested for leaks. A 1-decene monomer flow rate, chosen in the range of 700–2300 grams per hour, a reactor temperature of 75° C. and a reactor pressure of 30 psig were controlled throughout the reaction period. The reactor had a $BF_3$ gas cap and its liquid volume was controlled through a level control device at approximately one half of the reactor volume. The promoter, n-butanol or denatured ethanol, was added to a concentration of 0.25 wt. % based on feed. The reaction product was discharged to a low pressure flash tank to remove the gaseous material. The liquid product stream was then subjected to the neutralization and washing steps. The product was further treated by hydrogenation and fractionation. The resulting dimer fraction generally had a 97+% purity based on the gas chromatography method for oligomer distribution. A mixture of the dimer fractions from both the batch and the continuous reactor systems was used as a control and for the spiking study.

Example 2

$C_8$ Dimer

A reaction system with continuous monomer, 1-octene, feed and two-reactors in series was used in this example. The mechanical setup of both reactors was similar as described in Example 1. The effluent from the first reactor was introduced to the second. The second reactor was hydraulicly full. Temperature of both reactors were controlled at 50° C. and the pressure of the first reactor was controlled at 40 psig. Due to the pressure drop between the two reactors, the pressure in the second reactor was slightly lower than that of the first, generally less than a 1 psig differential. The promoters, methanol and 4-hydroxy-4-methyl-2-pentanone, were added continuously to the first reactor at a concentration of 0.1 wt. % and 0.65 wt. % respectively, based on feed. The reaction product was discharged to a low pressure flash tank to remove the gaseous material. The liquid product stream was then subjected to neutralization and washing steps. The product was further treated by hydrogenation and fractionation. The resultant dimer fraction generally had a 97+% purity based on the gas chromatography method for oligomer distribution. A mixture of the dimer fractions from the continuous reactor system was used as a control and for the spiking study.

Example 3

$C_{12}$ Dimer

The dimer sample was obtained from the operation of two large continuous stirred tank reactors in series. The monomer feed contained 98% 1-dodecene and 2% 1-decene. The reactor pressure was controlled at 30 psig and the reactor temperature at 32° C. The reaction product and unreacted monomer were separated by distillation. The dimer-rich fraction from the distillation was hydrogenated. After saturation, a sample of the dimer-rich fraction was further fractionated to obtain 97+% purity.

Example 4

$C_{14}$ Dimer

The oligomerization reaction was carried out in an autoclave reactor as described in Example 1. Two batch reactions were made to produce oligomer samples. In the first run, five-hundred grams of 1-tetradecene was charged into the reactor. The promoters, methanol and 4-hydroxy-4-methyl-2 pentanone, were added to a concentration of 0.05 wt. % and 0.25 wt. % of feed, respectively. The entire reactor was heated under a nitrogen blanket to reach 75° C. When the reactor temperature reached equilibrium, the reactor was then evacuated to remove the nitrogen. Boron trifluoride gas was then sparged slowly with agitation and temperature control via a cooling coil to avoid reactor temperature overrun. Additional boron trifluoride was added as necessary to maintain a reactor pressure of 20 psig. The reaction was terminated after two hours by venting off excess boron trifluoride gas and purging with nitrogen. The reaction product was then washed with a 4 wt. % aqueous sodium hydroxide solution followed by several water washes to ensure neutralization. In the second run, one-thousand grams of 1-tetradecene was charged into the reactor. The promoter, acetol, was added to a concentration of 0.125 wt. % of feed. Other operating conditions were identical to those cited in the first run except for the reactor temperature, which was maintained at 60° C., and the reactor pressure, which was 30 psig. The reaction products from the two runs were combined. The resultant product was further treated by hydrogenation and fractionation. The resultant dimer fraction generally had a 97+% purity.

Example 5

Formation and Filtration of Crystals

A sample of relatively poor quality decene based hydrogenated dimer, as characterized by a −54° C. of 1784 cSt, was placed into a temperature controlled bath at −30° C. Shortly after placing the sample into the bath a haze developed; after 24 hours crystalline material was observed. The crystals were allowed to continue to grow over a period of two weeks. However, it was observed that the crystals would quickly disappear if removed from the −30° C. bath. Subsequently, we discovered that the crystals were dissolved by the bulk fluid as it warmed.

Figure 1B:
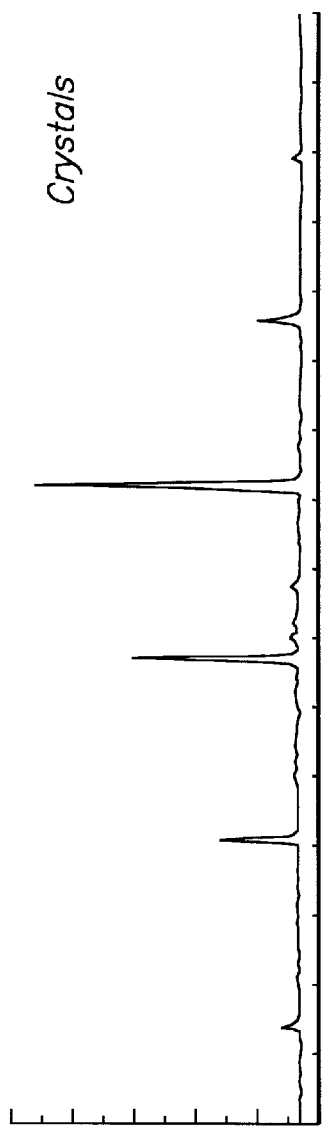

The sample was placed into a glove box that was temperature controlled to −45° C. in order to isolate the crystals for identification while preventing their dissolution. The glove box allowed the crystals to be vacuum filtered and washed with hexane in the cold environment. The apparatus and materials were allowed to achieve temperature equilibrium within the glove box at −45° C. Subsequently, gas chromatographic analysis was performed on the crystals which once isolated were stable and did not quickly melt at ambient temperatures. The gas chromatographic analysis revealed, upon comparison to standards (see FIG. 1), that the crystals eluted identically to normal paraffin standards which have a molecular weight corresponding to hydrocarbons having from 17 to 22 carbon atoms in length. The predominant component was identified as normal eicosane (20 carbon atoms).

Figure 2:
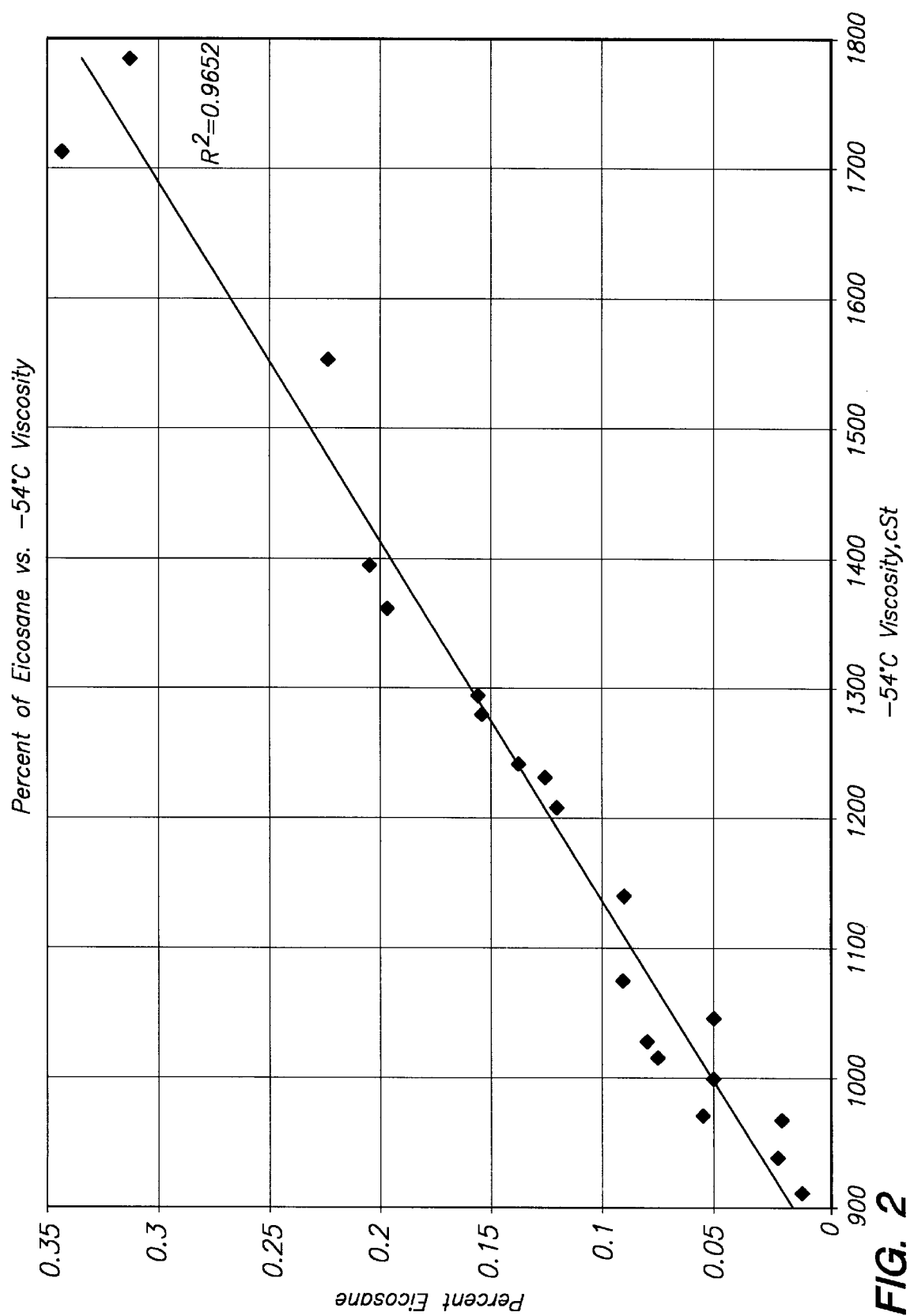
FIG. 2 is a plot of the weight percent normal eicosane in the dimer versus the −54° C. kinematic viscosity, which is also discussed in Example 5.

Several samples were analyzed by gas chromatography and their −54° C. kinematic viscosity measured. These samples consisted of 1-decene hydrogenated dimers prepared both from batch and continuous modes of formation. The results from the gas chromatographic analysis and the −54° C. kinematic viscosity are plotted in FIG. 2. The −54° C. viscosity increases proportionally to the concentration of the normal eicosane, even at very low concentrations.

Various amounts of pure normal paraffins were added to hydrogenated dimers of 1-octene, 1-decene, 1-dodecene and 1-tetradecene, separately. Each paraffin was added to the corresponding hydrogenated dimer, i.e. eicosane to the 1-decene hydrogenated dimer and tetracosane to the 1-dodecene hydrogenated dimer.

Example 6

Spiking of 1-Octene Dimers

Table 1 shows the results from adding various amounts of hexadecane to the 1-octene hydrogenated dimer. The samples were examined by gas chromatographic analysis for the percent n-paraffin and the −54° C. kinematic viscosity measured. The difference between the analysis and the amount added is due to the amount of normal paraffin present in the sample before any addition.

TABLE 1

Spiking Study for 1-Octene Hydrogenated Dimer

| −54° C. Viscosity, cSt | Amount of n-Hexadecane Added, % | Total n-Hexadecane by GC, % |
|---|---|---|
| 245 | 0.0 | 0.04 |
| 243 | 0.1 | 0.14 |
| 260 | 0.4 | 0.46 |
| 399 | 1.0 | 1.06 |

Example 7

Spiking of 1-Decene Dimers

Example 6 was repeated except n-eicosane and 9-methylnonadecane were used for spiking the 1-decene hydrogenated dimers. The samples were analyzed by gas chromatography for the percentages of the n-paraffin and the −40° C. and −54° C. kinematic viscosities were measured. The results are shown in Tables 2 and 3 for the n-eicosane and 9-methylnonadecane spiking, respectively.

TABLE 2

Spiking of 1-Decene Hydrogenated Dimer with n-Eicosane

| −54° C. Viscosity, cSt | −40° C. Viscosity, cSt | Amount of n-Eicosane Added, % | Total n-Eicosane by GC, % |
|---|---|---|---|
| 975 | 227 | 0.0 | 0.017 |
| 1253 | 231 | 0.1 | 0.115 |
| 2898 | 404 | 1.0 | 1.030 |

TABLE 3

Spiking of 1-Decene Hydrogenated Dimer with 9-Methylnonadecane

| −54° C. Viscosity, cSt | −40° C. Viscosity, cSt | Amount of 9-Methylnonadecane Added, % | Total 9-Methylnonadecane by GC, % |
|---|---|---|---|
| 975 | 227 | 0.0 | 0.518 |
| 971 | 230 | 0.1 | 0.609 |
| 1055 | 228 | 1.0 | 1.440 |

Example 8

Spiking of 1-Tetradecene Dimers

Example 6 was repeated except n-octacosane was used for spiking the 1-tetradecene hydrogenated dimers. The samples were analyzed by gas chromatography for the percent n-paraffin and the −20° C. kinematic viscosity measured. The results are shown in Table 4.

TABLE 4

Spiking Study for 1-Tetradecene Hydrogenated Dimer

| −20° C. Viscosity, cSt | Amount of n-Octacosane Added, % | Total n-Octacosane by GC, % |
|---|---|---|
| 342 | 0.0 | 0.05 |
| 3177 | 0.1 | 0.16 |

Example 9

Residence Time Effects on Dimer Quality

The samples were prepared as in Example 1 except the promoter was ethanol. The residence time was varied and listed in Table 5. The amount of n-eicosane was determined by gas chromatography and the −54° C. kinematic viscosity was measured.

TABLE 5

Residence Time Effect on n-Eicosane Content

| Residence Time, min | −54° C. Viscosity, cSt | n-Eicosane, % |
|---|---|---|
| 30 | 911 | 0.012 |
| 45 | 1047 | 0.050 |

The examples show that surprisingly small amounts of the respective normal paraffins can greatly affect the low temperature viscosities of the hydrogenated dimers. Generally, it had been previously believed that normal paraffins did not exist in the hydrogenated olefin oligomers. In fact, methyl branched isomers were previously identified to deleteriously effect the low temperature viscosities. While this is true, we have found that the effect of the normal paraffins is significantly greater, overshadowing the effect of the methyl paraffins. Hence, it is of the utmost importance to limit the concentration of n-paraffins in the hydrogenated dimer products.

In the process of investigating this invention, we found one hydrogenated 1-decene dimer from a third party which did have a −54° C. viscosity of 970 cSt and 0.056% n-eicosane. This sample appears to be the only one of its kind and we have no indication that this sample has been or could be reproduced. Until now, the production of routinely good quality 1-decene hydrogenated dimer has not been controllable. Now that we have discovered the true cause of poor low temperature performance, we are able to routinely produce hydrogenated dimers that have superior low temperature performance.

While the present invention has been described with reference to specific embodiments, this application is intended to cover those various changes and substitutions that may be made by those skilled in the art without departing from the spirit and scope of the appended claims.

What is claimed is:

1. A mixture of isomers of hydrogenated 1-octene dimer composition comprising at least 97.0 weight % hydrogenated 1-octene dimer and having less than 0.50 weight % normal hexadecane, and having a −54° C. viscosity of less than 280 cSt.

2. A hydrogenated 1-octene dimer composition according to claim 1 wherein the 1-octene dimer composition has less than 0.1 weight % normal hexadecane, and has a −54° C. viscosity of less than 250 cSt.

3. A mixture of isomers of hydrogenated 1-decene dimer composition comprising at least 97.0 weight % hydrogenated 1-decene dimer and having less than 0.05 weight % normal eicosane, having a −54° C. viscosity of less than 1000 cSt, and having a −40° C. viscosity of less than 231 cSt.

4. A hydrogenated 1-decene dimer composition according to claim 3 wherein the 1-decene dimer composition has less than 0.03 weight % normal eicosane.

5. A mixture of isomers of hydrogenated 1-tetradecene dimer composition comprising at least 97.0 weight % hydrogenated 1-tetradecene dimer and having less than 0.10 weight % normal octacosane, and having a −20° C. viscosity of less than 1000 cSt.

6. A hydrogenated 1-tetradecene dimer composition according to claim 5 wherein the 1-tetradecene dimer has less than 0.06 weight % normal tetracosane, and has a −20° C. viscosity of less than 500 cSt.

* * * * *